United States Patent [19]

Matson

[11] Patent Number: 4,552,013
[45] Date of Patent: Nov. 12, 1985

[54] ELECTROCHEMICAL SYSTEM

[75] Inventor: Wayne R. Matson, Ayer, Mass.

[73] Assignee: ESA, Inc., Bedford, Mass.

[21] Appl. No.: 586,079

[22] Filed: Mar. 5, 1984

Related U.S. Application Data

[60] Continuation-in-part of Ser. No. 465,786, Feb. 10, 1983, Pat. No. 4,497,199, which is a division of Ser. No. 241,945, Mar. 9, 1981, Pat. No. 4,413,505, and a continuation-in-part of Ser. No. 425,183, Sep. 28, 1982, , which is a division of Ser. No. 111,917, Jan. 14, 1980, Pat. No. 4,404,065.

[51] Int. Cl.$^4$ ................................. G01N 31/06
[52] U.S. Cl. ................. 73/61.1 C; 204/411; 422/70; 436/161
[58] Field of Search ................. 73/61.1 C; 204/400, 204/410, 411, 412, 180 G; 210/198.2, 656; 422/70; 436/161

[56] References Cited

U.S. PATENT DOCUMENTS 4,302,315 11/1981 Stetter et al. ................... 204/412

FOREIGN PATENT DOCUMENTS 2536394 3/1976 Fed. Rep. of Germany ... 73/61.1 C

OTHER PUBLICATIONS

Schieffer, G. W., *Pre-Column Electrochemical Cell for High-Performance Liquid Chromatography*, in Analyt. Chem., vol. 51 (9), pp. 1573-1575, Aug. 1979.

Primary Examiner—Stewart J. Levy
Assistant Examiner—Joseph W. Roskos
Attorney, Agent, or Firm—Hayes Davis & Soloway

[57] ABSTRACT

A coulometric flow cell having a defined flow path, and a working electrode in the form of a porous conductive matrix of a selected electro-conductive material in finely divided or powdered form, confined within a segment of the flow path, is described. The cell has particular utility for use with a liquid chromatography separation, and when placed in line upstream of sample injection, will remove selected electroactive components in the carrier fluid, and thereby reduce background level of contaminants reaching the column and eluting from the column. The cell may also be placed in line following sample injection whereby it may be employed to electrochemically modify selected materials in the mobile phase whereby to change their chromatographic characteristics. The cell also may be advantageously employed for direct testing or measuring of a sample solution.

18 Claims, 8 Drawing Figures

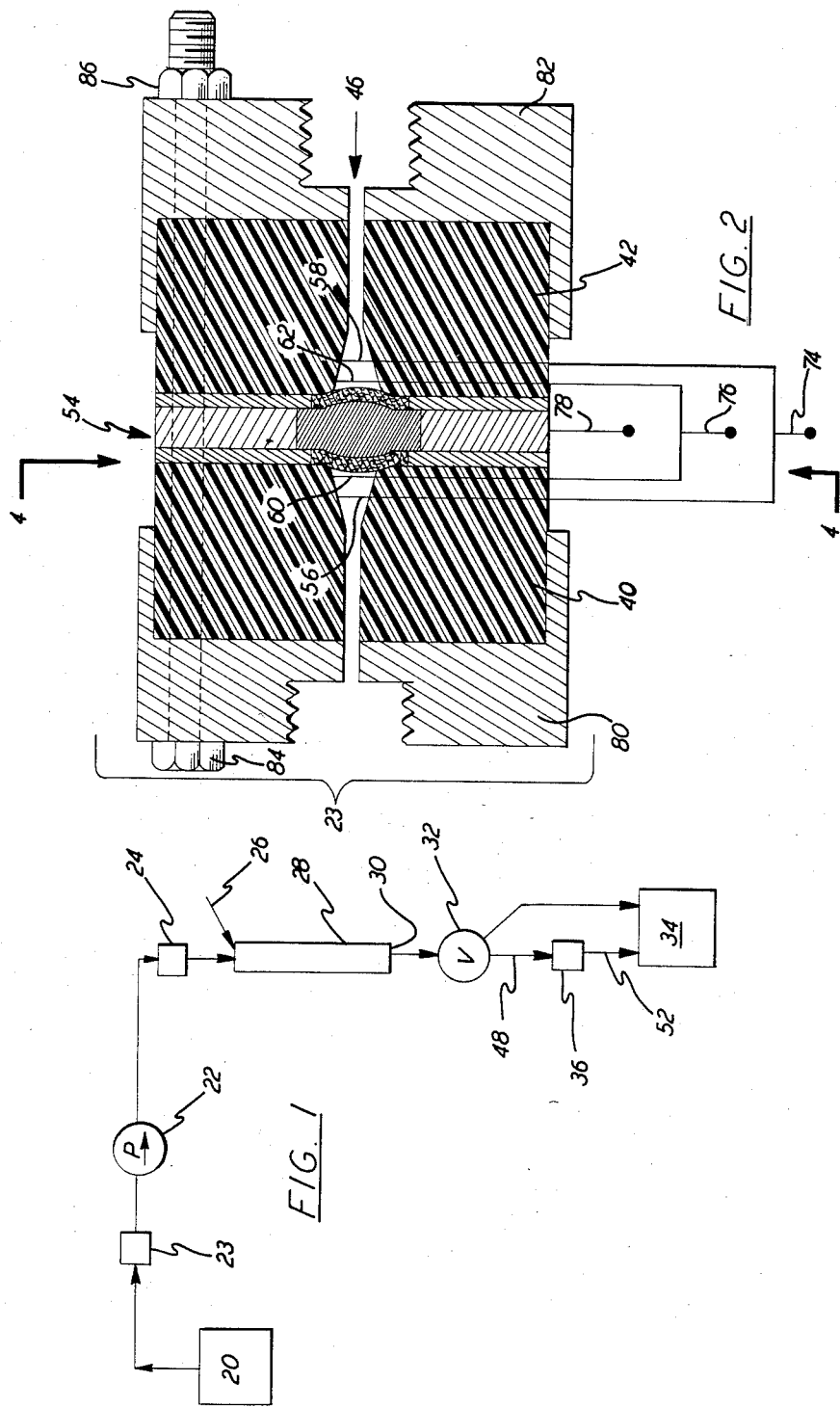

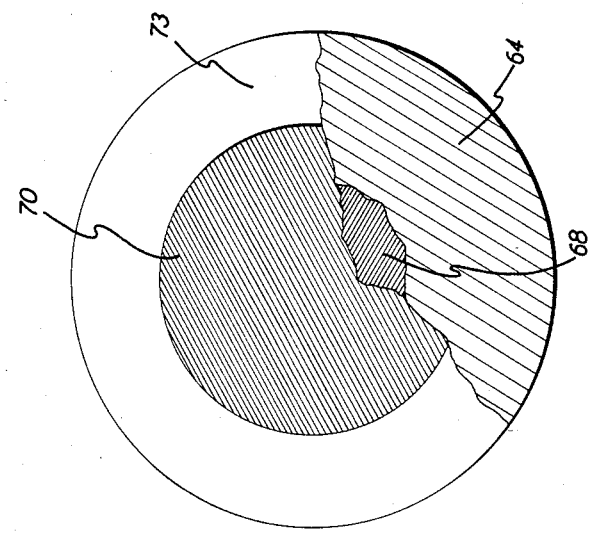
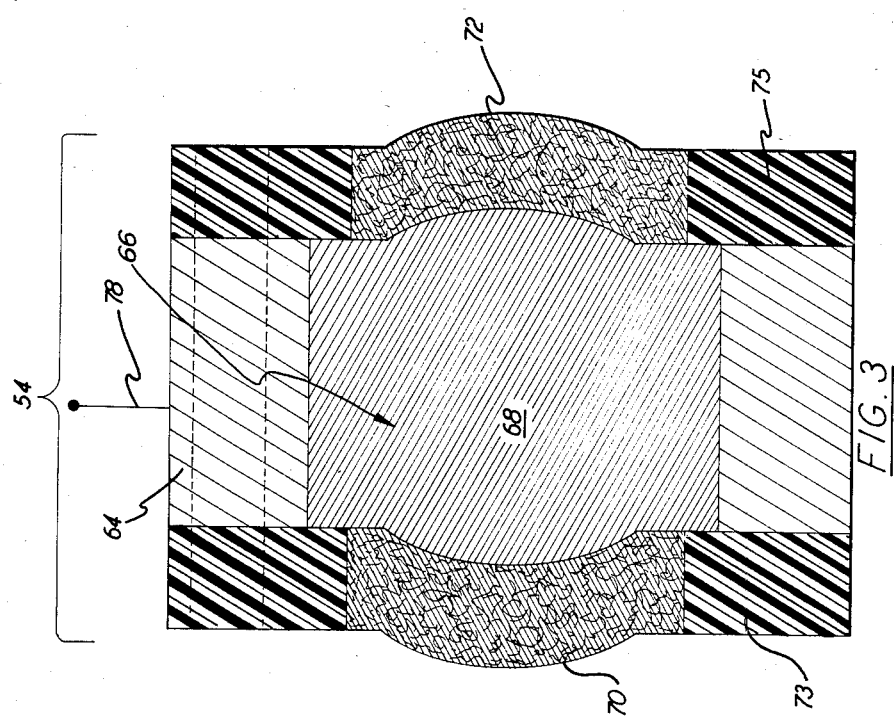

ELECTROCHEMICAL SYSTEM

This application is in part a continuation-in-part of my copending application Ser. No. 465,786 filed Feb. 10, 1983, now U.S. Pat. No. 4,497,199, which is in turn a divisional of application Ser. No. 241,945 filed Mar. 9, 1981, now U.S. Pat. No. 4,413,505, issued Nov. 8, 1983; and in part a continuation-in-part of my copending application Ser. No. 425,183, filed Sept. 28, 1982, which is in turn a divisional of application Ser. No. 111,917, filed Jan. 14, 1980, now U.S. Pat. No. 4,404,065, issued Sept. 13, 1983.

This invention relates to analytical systems for qualitatively and quantitatively testing materials in solution. The invention has particular utility for use as a guard cell in a liquid chromatography system and will be described particularly in connection with such utility. It will be seen from the following disclosure, however, that the invention also will have utility as an electrochemical cell for detecting the presence of and/or measuring the concentration of various substances of interest in sample solutions suspected of containing the selected substances.

Liquid chromatography is a well-known analytical technique in which a sample material is separated into its component species by dissolving the sample material in a carrier fluid to form a mobile phase which is then passed continuously through a solid phase. Generally, the solid phase comprises a bed of ion exchange resins or silica bonded to an organic molecule in powder or bead form, arranged in a stack or column. The various species contained in the sample material separate as a result of their different values of attraction for the various packing materials (ion exchange resins) in the bed to produce a so-called eluant solution which is then passed through a detection device. Classically, detection devices for liquid chromatography have been based on measurements of optical phenomena such as differences in indices of refraction or ultraviolet absorption of the varous species in the chromatographic eluant.

Two prerequisites for commercial chromatography systems are (1) sharp separation by the solid phase of the varous species in the sample so that individual species will appear at different times in the eluant, i.e. the sample is resolved into its component species; and (2) convenient means of continuously and accurately detecting and analyzing the separated species in the eluant. At the current state of the art chromatographic separation generally can be achieved at a level of selectivity that is substantially more precise than the level of sensitivity of detection achievable using classical optically based detection devices. More recently, detection devices based on electrochemical measurements have been proposed for use in connection with liquid chromatography separations. One such proposed electrochemical detection device employs a hanging drop mercury electrode suspended in the eluant solution. However, as noted in U.S. Pat. No. 3,706,381, detectors employing hanging drop mercury electrodes have not proved to be entirely satisfactory due to the considerable noise associated with the dropping mercury. It also has been proposed to employ solid electrodes for directly measuring species in an eluant solution. One such proposed device employs a test electrode in the form of a solid graphite button or a carbon or graphite paste flat plate for contacting the eluant stream from a liquid chromatography column. However, electrochemical detection devices of this type generally are able to achieve sensitivity of 100 picograms at best, and may suffer from decay of sensitivity. Also, while electrochemical detection devices employing carbon or graphite paste electrodes may function well for many applications of reverse-phase chromatography, problems can develop when nonaqueous solvents are used due to the combination of a high volume flow rate with the mechanical instability of the carbon paste matrix. In addition, the presence of dissolved impurities (e.g. dissolved oxygen, halides, trace metals, etc.) in the mobile phase and/or sample can severely limit the performance of an electrochemical detector.

In my aforesaid U.S. Pat. No. 4,404,065, I disclose an electrochemical detection apparatus of extreme sensitivity which essentially comprises a flow-cell having at least one active testing electrode, at least one reference electrode, and at least one counter electrode. Each electrode comprises a liquid impervious solid body having a bore extending therethrough with the electrode active surface located in the bore. As disclosed therein, the active testing electrode typically comprises disks of suitable electrode base material such as carbon, graphite or platinum. Alternatively, the active testing electrodes may comprise disks of chemically inert, electrically insulating material such as a synthetic polymeric plastic, having coatings of active electrode material such as mercury, gold, silver, bismuth, $PbO_2$, $MnO_2$ or other suitable electrode material. The electrodes are arranged in a stack, electrically insulated from one another with their respective bores aligned so as to define a flow channel through which liquid to be detected can be passed. Various electrochemical responses are achieved by varying the construction, number and arrangement of electrodes in the stack, and the potentials applied to the electrodes. While the electrochemical detection apparatus of my aforesaid U.S. Pat. No. 4,404,065 overcomes many of the aforesaid problems of the prior art certain materials of interest cannot readily be detected and measured using carbon or graphite, etc., electrodes. Moreover, problems still subsist due to interference signals from dissolved impurities in the mobile phase, and/or insufficient separation of species in the chromatography column.

In order to overcome this latter problem, I disclose in my aforesaid U.S. Pat. No. 4,413,505 the use of an amperometric guard cell in-line in a chromatography system for removing and/or modifying electroactive materials in the carrier fluid and/or mobile phase and to reduce background level of contaminants reaching the chromatography column and eluting from the column, and/or to modify the chromatographic characteristics of related materials in the mobile phase. The present invention provides an improvement in electrochemical detection and/or guard cells.

It is thus a primary object of the present invention to provide a novel and improved electrochemical system, i.e. method and apparatus, which overcomes the aforesaid and other problems and limitations of the prior art.

In order to effect the foregoing and other objects, there is provided a high efficiency electrochemical cell comprising a flow cell defining a flow path having at least one working electrode, at least one counter electrode, and at least one reference electrode, all operatively disposed, electrically insulated from one another, within the flow path of the cell. The working electrode comprises a porous matrix of a selected electrically conductive material in finely divided or powder form, confined within a segment of the flow path of the cell. In preferred embodiment of the invention the cell is positioned in-line in a chromatography apparatus upstream of the chromatography column. In such embodiment the electrochemical cell, which may be constructed to operate under high pressure conditions existing on the upstream side of the chromatography column may be employed to remove selected electroactive species present in the sample or mobile phase to reduce the background level of contaminants reaching the column, and/or to change chromatographic characteristics of selected species in the mobile phase to permit chromatographic separations that might otherwise be impossible. For example, the electrochemical cell may be used as a guard cell to remove dissolved oxygen from the mobile phase and/or sample, thereby permitting reductive liquid chromatography and electrochemical analysis of the sample.

Yet other objects of the invention will in part appear obvious and will in part appear hereinafter. The invention accordingly comprises the apparatus processing the construction, combination of elements, and arrangement of parts, and the processes comprising the several steps and relation of one or more of such steps with respect to each of the others, all of which are exemplified in the following detailed description, and the scope of the application as will be indicated in the claims.

For a fuller understanding of the nature and objects of the present invention reference should be had to the following detailed description taken in connection with the accompanying drawings wherein:

FIG. 1 is a schematic view of one form of liquid chromatography apparatus incorporating a coulometric cell in accordance with the present invention as a guard cell;

FIG. 2 is a side elevational view, partly in section, showing details of a preferred form of coulometric cell in accordance with the present invention;

Figure 5:
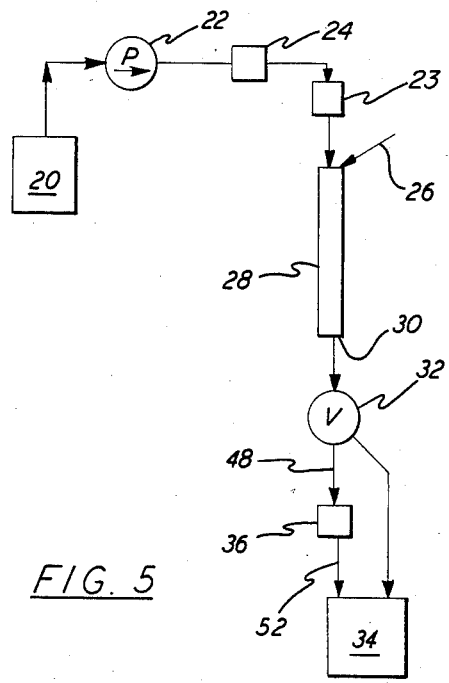
Figure 6:
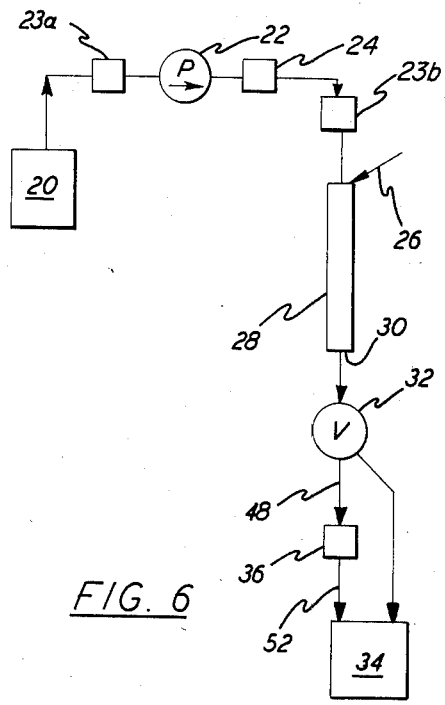
Figure 7:
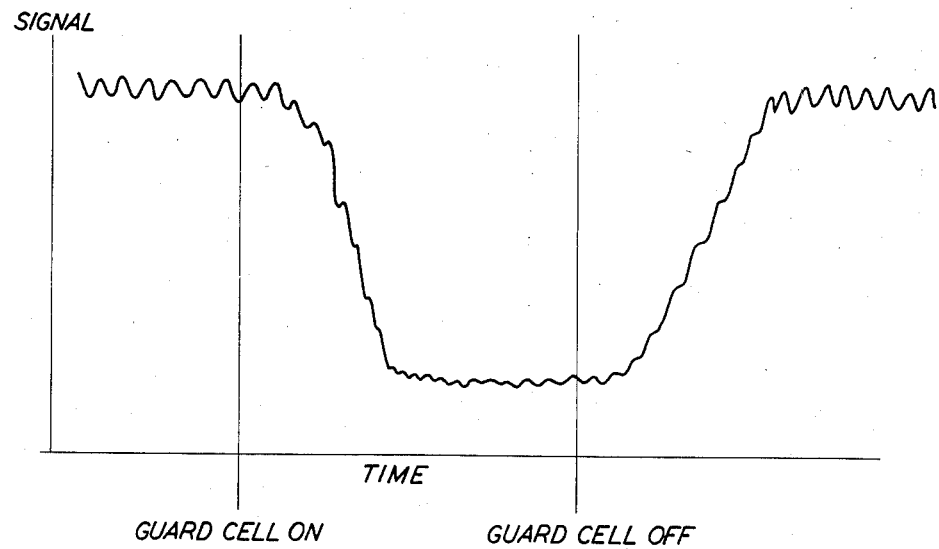
Figure 8:
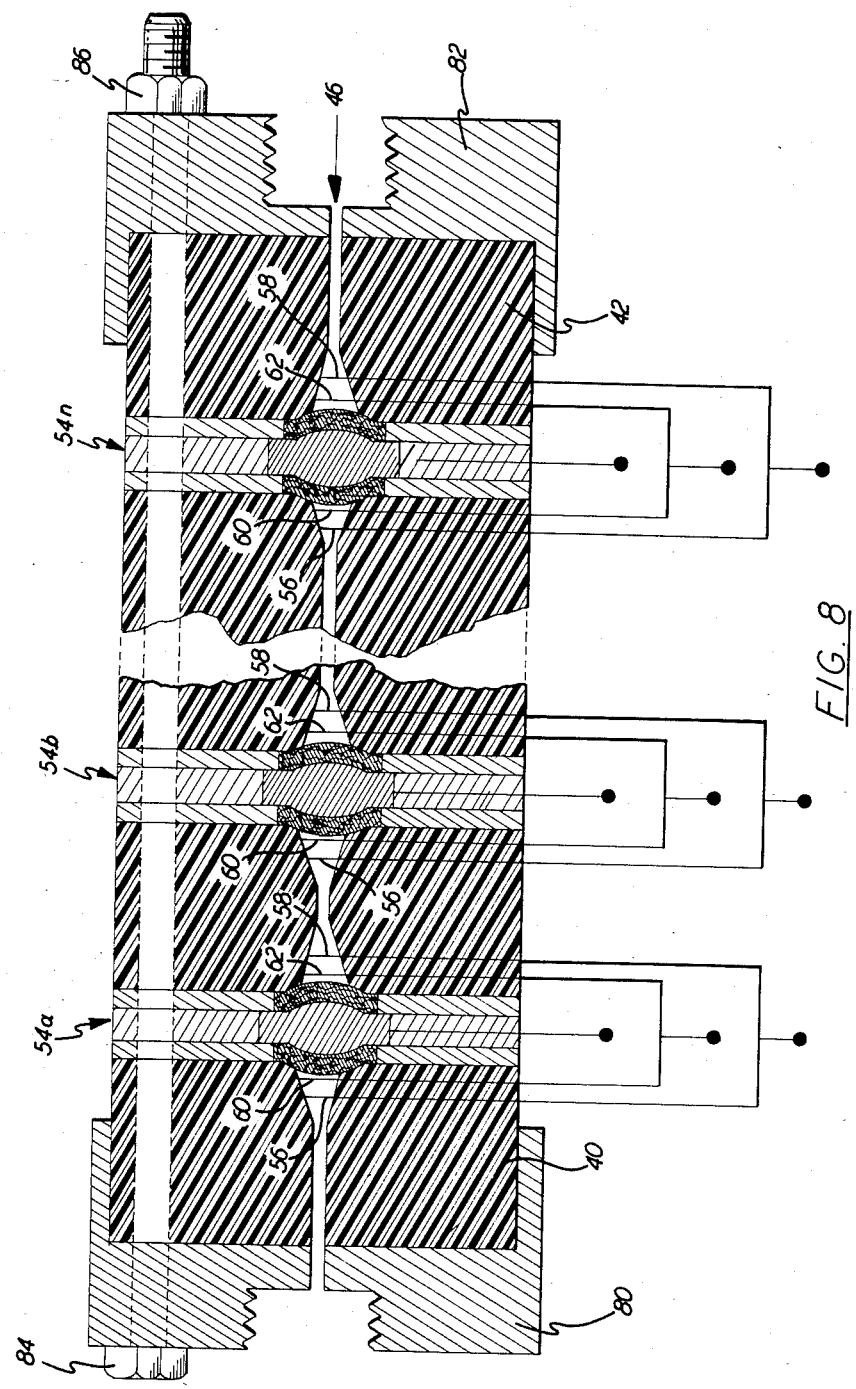

FIG. 3. is a cross sectional view of the coulometric cell of FIG. 1, showing details of the working electrode portion of the cell;

FIG. 4 is a side elevational view, in cross section, taken along line 4—4, of the electrode of FIG. 3; showing details of the working electrode portion of the cell;

FIG. 5 is a schematic view of an alternative liquid chromatography apparatus employing the coulometric cell of FIG. 2 as a guard cell in accordance with the present invention;

FIG. 6 is a schematic view of still another alternative form of liquid chromatography apparatus employing two coulometric cells of FIG. 2 as guard cells in accordance with the present invention;

FIG. 7 is a chart recording showing measurements made on the eluant from a liquid chromatography apparatus and illustrating the advantages of the present invention; and FIG. 8 is a fragmented side elevational view, partly in section, showing details of an alternative form of coulometric cell in accordance with the present invention.

Further understanding of the features and advantages of the present invention will be had from the following detailed description of the invention which illustrates a preferred form of coulometric cell of the present invention in combination with a liquid chromatography separation apparatus and a separate electrochemical detection cell. It will be understood, however, that the coulometric cell of the present invention may be advantageously employed in combination with a liquid chromatography separation apparatus employing a conventional optical detection device. The coulometric cell of the present invention also may be advantageously employed for making direct electrochemical measurements of sample solutions.

Referring to FIG. 1, there is illustrated a liquid chromatography apparatus incorporating a coulometric cell made in accordance with the present invention as a guard cell. The illustrated liquid chromatography apparatus includes a mobile phase reservoir 20 coupled through a constant volume pump 22, a coulometric cell 23 (as will be described in detail hereinafter), and an injection valve 24 and sample inlet 26 to the top of a liquid chromatography column indicated generally at 28. In practice, sample materials to be tested are introduced into the chromatography apparatus either by direct injection of microliter amounts of sample material into the chromatography column 28, e.g. through a syringe at sample inlet 26, or the sample material may be introduced into the chromatography column 28 as a dilute solution of sample material at injection valve 24. Thus, if desired, either injection valve 24 or sample inlet 26 may be omitted from the system. Chromatography column 28 is packed with selected ion exchange resins in bed or powder form. The section of the mobile phase, and the selection and packing order of the ion exchange resins will depend on the particular separations desired and can readily be determined by one skilled in the art and thus will not further be described herein. The base of chromatography column 28 is coupled via an outlet 30 to a splitter valve 32 which divides the eluant from the chromatography column 28 between a sample collection vessel or waste container 34 and a detection device indicated generally at 36.

The illustrated chromatography apparatus (less coulometric cell 23) is conventional and may be of the type described by P. H. Freeman and W. L. Zielinski in U.S. Bureau of Standards Technological Note Number 589, Page 1 (July 1980 to June 1979).

Referring to FIGS. 2 to 4, the coulometric cell 23 in accordance with the present invention comprises an electrochemical flow cell comprising a hollow cylindrical two part body 40, 44 formed of a rigid, liquid impervious, electrically insulating, chemically inert material such as a synthetic polymeric material, e.g. an unplasticised polyvinyl chloride, polypropylene, a polytetrafluoroethylene fluorocarbon resin such as Teflon, Kel-F, Halar, Fluoron, or other commercially available polymeric material. Cylindrical body 40, 44 defines, in part, an elongate cylindrical flow path 46 in which are located the reference, counter and working electrodes of coulometric cell 23, as will be described in detail hereinafter.

Coulometric cell 23 preferably has at least one working electrode, at least one reference electrode and at least one counter electrode. A preferred form of cell 23 shown in FIGS. 2 to 4 comprises five electrically discrete electrode elements arranged as follows:—a working electrode 54, two counter electrodes 56 and 58, and two reference electrodes 60 and 62.

Counter electrodes 56 and 58 may comprise frits of porous electrode base material, but preferably counter electrodes 56 and 58 comprise inert metal terminals such as one or a plurality of palladium or platinum wires. Reference electrodes 60 and 62 preferably comprise inert metal terminals such as one or a plurality of palladium, palladium oxide or platinum wires. Preferably, reference electrodes 60 and 62 are closely spaced from and equidistant from working electrode 54, while counter electrodes 56 and 58 may be located further away from working electrode 54.

Counter electrodes 56 and 58, and reference electrodes 60 and 62 are connected, in known manner, via suitable electrical conductors such as palladium or platinum wires 74 and 76, respectively, which extend through suitable pressure tight fittings in the side walls of body 40, 44 to sources of controlled reference and counter potentials, respectively.

A feature and advantage of the present invention resides in the provision of a coulometric cell of enhanced efficiency, selectivity and sensitivity. This is achieved, in part, by providing a working electrode 54 with a porous conductive matrix comprising a selected electrically-conductive material 68 in finely divided or powdered form, confined within a segment of the flow path 46 of the cell. More particularly, in accordance with a preferred embodiment of the invention, working electrode 54 comprises a ring or short, flat hollow cylindrical member 64 formed of a chemically inert (to the materials to which the cell will be exposed), material. Ring member 64 may be formed of an electrically conductive material such as stainless steel, gold plated stainless steel, platinum, or other chemically inert metal. Alternatively, ring member 64 may be formed of a chemically inert dielectric material such as Teflon or other commercially available polymeric material. Ring member 64 central aperture 66 is aligned with the flow path 46 of the cell so that the ring member 64 defines the flow path 46 for a portion of its length.

A mass of a selected finely divided electrically conductive material, e.g. in powder, spherical or flaked form is held within aperture 66. Conductive material 68 should be electrically conductive, chemically inert (to the materials to which the cell will be exposed), and should have a desired selectivity and sensitivity for the materials to which it will be exposed. Material 68 may comprise a conventional electrode material such as a powdered or flaked metal, for example, gold, platinum, nickel, silver, bismuth, or lead. Material 68 also may comprise an alloy or amalgam, for example of platinum and gold, or of lead and bismuth, which are given as exemplary. Also useful as electrode material 68 are powdered oxides of metals such as $PbO_2$, $MnO_2$, and $SnO_2$, and powdered sulfides of metals such as PbS, MnS and SnS which also are given as exemplary. Still other materials not conventionally considered as electrode materials may be employed as conductive material 68, including finely divided conductive ion exchange polymers such as Acetylene Black/Doped polymeric sulfonated or aminated Styrene; conductive lead/lead dioxide, and conductive tin oxide, and immobilized enzyme conductive polymers such as Glucoronidase in Acetylene Black/Doped PVC, which are given as exemplary.

The finely divided, electrically conductive material 68 may have an average particle size of between about 2–3 microns and about 400 microns. For most applications electrically conductive material 68 generally will have an average particle size in the order of 10 microns or less.

Electrically conductive material 68 is confined within aperture 66 by means of porous membranes or frits, e.g. glass, glass fiber, polypropylene, porous Teflon, or the like 70, 72 which are located, one each to each side of ring 64. Alternatively, and particularly in cells in which electrically conductive material 68 comprises a powdered or flaked metal, porous membranes or frits 70, 72 may take the form of fine grids or screens of solid wire of the same metal of material 68. Porous membranes or frits 70 and 72 are mounted or compression fitted to gaskets or O-rings 73 and 75, respectively, formed of a chemically inert, electrical insulating material such as Teflon, Kel-F, polyethylene or the like.

Electrical contact to the electrically conductive material 68 may be provided by fixing a conductive wire 78 to the rim of ring 64 (when ring 64 is istelf electrically conductive), or by means of a wire or rod (not shown) which extends through a pressure tight fitting in the rim of ring 64 into the mass of electrically conductive material 68.

Conductive wire 78 in turn is connected in known manner to a source of a controlled working potential.

Completing guard cell 23 are a pair of rigid, high pressure resistent exterior housing members such as stainless steel cap members 80 and 82. The latter are jam fitted over the ends of body 40 and body 42, respectively. As seen in FIG. 2, stainless steel cap members 80 and 82 are provided with internally threaded fittings 84, 86 to permit connection of cell 23 to a fluid stream, e.g. the chromatography system as above described. The entire cell assembly is held together by three axial compression bolts, only one of which 84, is shown, which extend through suitably provided bolt holes in the stainless steel cap members 80 and 82 cell bodies 40 and 42, and the periphery of O-rings 73 and 75 and of working electrode 43 ring 64. Bolts 84 align the individual elements of the cell 23 and, when anchored with nuts 86, apply pressure to keep cell 23 together.

Cell 23 may be assembled as follows:—A first sub-assembly comprising inert body 40, cap member 80 and bolts 84 is stood on end, and a second sub-assembly comprising frit 70 and O-ring 73 assembly and ring 64 is placed on top of the first sub-assembly. Dry, powdered electrically conductive material is then loaded into aperture 66 in an amount calculated to produce a slight convexity of frits 70 and 72 when the cell is completely assembled and tightened. Frit 72 and O-ring 75 assembly is then placed on top of the loaded ring 64, and a third sub-assembly comprising cylindrical body 42 and cap member 82 is placed over the entire assembly. The nuts 86 are then screwed onto bolts 84, and the assembly tightened.

FIG. 1 shows the placement of coulometric cell 23 as a guard cell upstream of injection valve 24 in a chromatography system. With cell 23 located at this position in a chromatography system, it can, through appropriate selection of powdered electroactive material 68, and application of electrical potentials to the cell, act as a screen to remove selected electroactive materials in the mobile phase used to elute column 28, thus reducing background level of contaminants reaching the column and eluting from the column. This in turn may reduce background signals and thus enhance operation of the downstream detector device 36 and/or permit the use of certain mobile phase combinations with UV or fluorescent detectors which ordinarily could not be used with such detectors. Removal of certain contaminants also may increase column life.

FIG. 5 illustrates the placement of coulometric cell 23 immediately downstream of injection valve 24. With cell 23 located at this position in a chromatography system, it can, through appropriate selection of powdered electroactive material 68, and application of electrical potentials to the cell, electrochemically modify (i.e., oxidize or reduce selected materials injected into the column) thereby changing the material's chromatographic characteristics whereby to permit chromatographic separations that otherwise might be impossible.

FIG. 6 illustrates the placement of two coulometric cells 23A, 23B respectively, made in accordance with the present invention, in a chromatography system, upstream and downstream of injection valve 24. This embodiment provides both screening and materials modification.

Further understanding of the principles and advantages of the present invention may be had by reference to the following examples which illustrate the use of the electrochemical detection device in accordance with the present invention.

EXAMPLE I

A coulometric cell 23 made in accordance with FIGS. 2 to 4 was used. The cell comprised one working electrode 54 formed of powdered gold having a five (5) micron average particle size, two palladium oxide wire reference electrodes 60 and 62, and two palladium wire counter electrodes 56 and 58. Cell 23 was located in-line upstream of injection valve 24, i.e. as shown in FIG. 1, and was employed as a guard cell to remove dissolved oxygen from the mobile phase.

The basic procedure was to dissolve small amounts of sodium phosphate buffer in methanol water matrix (0.2% phosphate, 89.8% water, 10% methanol) to form an eluant solution. The sample solution was then introduced into a Model 6000 liquid chromatography system (available from Waters Associates). The chromatography column was packed with a C-18 column packing from Brownlee. (The manufacturer describes the packing as comprising an eighteen-carbon hydrocarbon on an inert carrier.) Flow rate through the chromatography column was 1 ml/min, with an inlet pressure of 1600 psi. The eluant from the chromatography column was run through an electrochemical detection cell (Model No. 5010, available from E.S.A., Inc., Bedford, Mass.). The electrical signal outputs from the electrochemical detection cell were recorded on an automatic recorder and shown in FIG. 7a with the coulometric (guard) cell 23 turned on (−0.50 v.) and off. As can be seen in FIG. 7 cell 23 provides substantial suppression of background signals.

Additional cells, similar to cell 23, set at other potentials may be included in line to further suppress background and/or to further modify selected materials to change their chromatographic characteristics.

As should be clear from the foregoing the inclusion of coulometric cell 23 in a liquid chromatography system in accordance with the present invention offers a number of advantages. Furthermore, coulometric cell 23 is not limited to use as a guard cell in liquid chromatography separations, but also may be advantageously employed for direct monitoring or measuring a variety of sample solutions, for example, of industrial, environmental, geophysical and biomedical interest.

It also will be appreciated that the invention is not limited to a coulometric cell having only one working electrode. Rather, a plurality of electrically discrete packed powder working electrodes 54a, 54b . . . as shown in FIG. 8, comprising the same or different electroactive materials, and operable at different selected potentials, may be assembled in series within a single electrochemical cell. Various electrochemical responses may be achieved by varying the construction and numerical arrangement of electrodes as taught herein, and the potentials applied to the various electrodes, as taught in my aforesaid U.S. Pat. No. 4,404,065.

The technique disclosed herein also may be advantageously used for producing coulometeric cells for specific ions measuring either or simultaneously capacitive changes, resistance changes and/or faradaic processes using specific metals, for example, bismuth for $PO_4$ measurement, or lead for sulfate measurement. Also, electrically conductive immobilized enzymes and electrically conductive ion exchange resins may advantageously be employed to give enhanced sensitivity and selectivity to specific biological compounds, for example glycosides such as Gigitoxin, Digoxin and Gitoxin, Endorphins and other polypeptides, sugars, and phosphatides (phospholipids) such as phosphatidyl choline (Lecithin), phosphatidyl etholamine, and phosphatide serine.

As will be apparent from the foregoing, the provision of electrochemical cells having packed powder working electrodes in accordance with the present invention provides exceptionally high area-to-volume ratios coupled with extremely small unstirred layers which assures rapid electrode response with extreme selectivity and sensitivity as compared to conventional prior art electrochemical cells. Still other features, modifications, advantages and objects will be obvious to one skilled in the art.

I claim:

1. An electrochemical flow cell for testing or treating a sample solution, said cell comprising:
   a holder assembly defining a flow path and having an inlet for directing a stream of said solution into said cell, and an outlet for directing treated solution from said cell; and,
   a plurality of electrode elements arranged in said holder, said electrode elements being operatively disposed, electrically insulated from one another, within said flow path, said plurality including at least one reference electrode, at least one counter electrode, and at least one working electrode, said at least one working electrode comprising a packed porous conductive matrix comprising a selected electrically-conductive material in finely divided or powdered form, confined within and restricting a segment of said flow path.

2. An electrochemcial flow cell according to claim 1, and including a pair of high pressure resistant fittings communicating with said flow path.

3. A flow cell according to claim 1, wherein said at least one working electrode comprises an electrically conductive, chemically inert, electrically conductive material selected from the group consisting of a powdered or flaked metal, a metal alloy, a metal oxide, and a metal sulfide.

4. A flow cell according to claim 3, wherein said electrode material comprises a metal selected from the group consisting of gold, platinum, nickel, silver, bismuth, lead, and an alloy of two or more of said metals.

5. A flow cell according to claim 3, wherein said electrode material comprises a metal oxide selected from the group consisting of $PbO_2$, $MnO_2$, and $SnO_2$.

6. A flow cell according to claim 3, wherein said electrode material comprises a metal sulfide selected from the group consisting of PbS, MnS and SnS.

7. A flow cell according to claim 3, wherein said at least one counter electrode and said at least one reference electrode each comprise an inert metal wire.

8. A flow cell according to claim 3, wherein said electrode material comprises a finely divided electrically conductive ion exchange polymer.

9. A flow cell according to claim 3, wherein said electrode material comprises an immobilized enzyme electrically conductive polymer.

10. A flow cell according to claim 1, wherein said at least one working electrode includes a liquid impervious ring member having a central aperture which defines in part said flow path, said finely divided electrically-conductive material being loaded within said ring central aperture and held therein by a pair of porous membranes or frits positioned, one each, to either side of said ring.

11. A flow cell according to claim 10, wherein said ring comprises an electrically conductive material, and including means affixing a conductive wire to the rim of said ring.

12. A flow cell according to claim 10, wherein said ring comprises a dielectric material, and including conductive means extending through the rim of said ring in contact with said porous conductive matrix.

13. A flow cell according to claim 1, comprising at least three electrode elements, at least one of said electrode elements being a working electrode, and including means for connecting said at least one working electrode to a controlled working potential; at least one other of said electrode elements being a reference electrode, and including means for connecting said at least one reference electrode to a reference potential; and at least yet one other of said electrode elements being a counter electrode, and including means for connecting said at least one counter electrode to a counter potential.

14. In a liquid chromatography apparatus having a chromatographic column through which a mobile phase can be passed wherein species in said mobile phase can be separated to produce an eluant fluid stream, the improvement which comprises a flow cell as defined by claim 1, in line upstream of said chromatographic column.

15. In a chromatography apparatus according to claim 14, and including injector means for injecting sample material into said mobile phase, the improvement wherein said flow cell is located upstream of said injector means.

16. In a chromatography apparatus according to claim 14, and including injector means for injecting sample material into said mobile phase, the improvement wherein said flow cell is located downstream of said injector means.

17. In a method of chromatographically analyzing a sample material wherein a sample is dissolved in a carrier fluid to form a mobile phase which then is passed through a chromatography column, electrochemically screening said carrier fluid to selectively remove electroactive materials therein by passing said carrier fluid through a flow cell as defined by claim 1, prior to injecting said sample material into said carrier fluid.

18. In a method of analyzing a sample material by liquid chromatography wherein said sample is dissolved in a carrier fluid to form a mobile phase which then is passed through a chromatography column, electrochemically treating said mobile phase by passing said mobile phase through a flow cell as defined by claim 1 prior to passing said mobile phase through said chromatography column, whereby to change chromatographic characteristics of selective materials therein.

* * * * *